United States Patent
Alghannam et al.

(10) Patent No.: US 11,517,892 B2
(45) Date of Patent: *Dec. 6, 2022

(54) METHODS OF PRODUCING ISOMERIZATION CATALYSTS

(71) Applicant: Saudi Arabian Oil Company, Dhahran (SA)

(72) Inventors: Afnan Alghannam, Khobar (SA); Sohel K. Shaikh, Dhahran (SA); Munir D. Khokhar, Al-Khobar (SA); Faisal H. Alshafei, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 310 days.

This patent is subject to a terminal disclaimer.

(21) Appl. No.: 16/701,793

(22) Filed: Dec. 3, 2019

(65) Prior Publication Data

US 2021/0162394 A1    Jun. 3, 2021

(51) Int. Cl.

| | | |
|---|---|---|
| *B01J 21/10* | (2006.01) | |
| *B01J 35/02* | (2006.01) | |
| *B01J 35/10* | (2006.01) | |
| *B01J 37/03* | (2006.01) | |
| *B01J 37/10* | (2006.01) | |

(Continued)

(52) U.S. Cl.
CPC .............. *B01J 37/031* (2013.01); *B01J 21/10* (2013.01); *B01J 23/02* (2013.01); *B01J 35/023* (2013.01); *B01J 35/1019* (2013.01); *B01J 37/0018* (2013.01); *B01J 37/08* (2013.01); *B01J 37/10* (2013.01); *C07C 4/06* (2013.01); *C07C 6/04* (2013.01); *C07C 11/06* (2013.01)

(58) Field of Classification Search
CPC ...... B01J 23/02; B01J 37/0018; B01J 37/031; B01J 37/08; B01J 37/10
See application file for complete search history.

(56) References Cited

U.S. PATENT DOCUMENTS

| | | |
|---|---|---|
| 2,947,708 A | 8/1960 | Wilson et al. |
| 3,546,313 A | 12/1970 | Banks |

(Continued)

FOREIGN PATENT DOCUMENTS

| | | | | |
|---|---|---|---|---|
| CA | 2771827 A1 | * | 3/2011 | ............. B01J 21/04 |
| CN | 101531558 A | | 9/2009 | |

(Continued)

OTHER PUBLICATIONS

Ding et al., Nanoscale Magnesium Hydroxide and Magnesium Oxide Pwoders: Control over Size, Shape and structure via Hydothermal Synthesis, Chem. Mater., 2001, 13:435-440.*

(Continued)

*Primary Examiner* — Jun Li (74) *Attorney, Agent, or Firm* — Dinsmore & Shohl LLP (57) ABSTRACT

Methods of producing an isomerization catalyst include preparing a catalyst precursor solution, hydrothermally treating the catalyst precursor solution to produce a magnesium oxide precipitant, and calcining the magnesium oxide precipitant to produce the isomerization catalyst. The catalyst precursor solution includes at least a magnesium precursor, a hydrolyzing agent, and polyethylene glycol. Methods of producing propene from a butene-containing feedstock with the isomerization catalyst and a metathesis catalyst are also disclosed.

7 Claims, 5 Drawing Sheets

(51) Int. Cl.
  *C07C 4/06* (2006.01)
  *C07C 6/04* (2006.01)
  *B01J 23/02* (2006.01)
  *B01J 37/00* (2006.01)
  *B01J 37/08* (2006.01)
  *C07C 11/06* (2006.01)

(56) References Cited

U.S. PATENT DOCUMENTS

| | | |
|---|---|---|
| 3,586,731 A | 6/1971 | Heckelsberg |
| 3,702,886 A | 11/1972 | Argauer et al. |
| 4,024,201 A | 5/1977 | Takahashi |
| 4,071,471 A | 1/1978 | Banks et al. |
| 4,575,575 A | 3/1986 | Drake et al. |
| 4,609,769 A | 9/1986 | Kukes et al. |
| 4,684,760 A | 8/1987 | Drake |
| 5,026,935 A | 6/1991 | Leyshon et al. |
| 5,026,936 A | 6/1991 | Leyshon et al. |
| 5,053,379 A | 10/1991 | Giordano et al. |
| 5,153,165 A | 10/1992 | Lowery et al. |
| 6,207,115 B1 | 3/2001 | Chodorge et al. |
| 6,538,168 B1 | 3/2003 | Schwab et al. |
| 6,586,649 B1 | 7/2003 | Botha et al. |
| 6,646,172 B1 | 11/2003 | Schwab et al. |
| 6,777,582 B2 | 8/2004 | Gartside et al. |
| 6,875,901 B2 | 4/2005 | Gartside et al. |
| 6,977,321 B1 | 12/2005 | Dath et al. |
| 7,214,841 B2 | 5/2007 | Gartside et al. |
| 7,604,794 B2 | 10/2009 | Tiitta et al. |
| 7,608,746 B2 | 10/2009 | Setoyama et al. |
| 7,754,647 B2 | 7/2010 | Schubert et al. |
| 7,754,934 B2 | 7/2010 | Tsunoda et al. |
| 7,977,522 B2 | 7/2011 | Takai et al. |
| 8,100,996 B2 | 1/2012 | Simmons et al. |
| 8,299,313 B2 | 10/2012 | Takai et al. |
| 8,324,440 B2 | 12/2012 | Popp et al. |
| 8,343,885 B2 | 1/2013 | Ruettinger et al. |
| 8,440,874 B2 | 5/2013 | Ramachandran et al. |
| 8,586,813 B2 | 11/2013 | Ramachandran et al. |
| 8,722,568 B2 | 5/2014 | Popp et al. |
| 9,630,167 B2 | 4/2017 | Bordoloi et al. |
| 9,834,497 B2 | 12/2017 | Shaikh et al. |
| 9,884,794 B2 | 2/2018 | Al-Khaffaf et al. |
| 10,005,703 B2 | 6/2018 | Abudawoud et al. |
| 10,017,873 B1 | 7/2018 | Koo et al. |
| 10,059,645 B2 | 8/2018 | Shaikh et al. |
| 10,065,906 B2 | 9/2018 | Shaikh et al. |
| 10,214,466 B2 | 2/2019 | Shaikh et al. |
| 10,550,048 B2 | 2/2020 | Alshafei et al. |
| 11,311,869 B2 * | 4/2022 | Alghannam ............ B01J 21/10 |
| 2004/0168367 A1 | 9/2004 | Suenaga et al. |
| 2004/0254411 A1 | 12/2004 | Steinbrenner et al. |
| 2005/0014981 A1 | 1/2005 | Gartside et al. |
| 2006/0293548 A1 | 12/2006 | Spamer et al. |
| 2007/0038010 A1 | 2/2007 | Xie et al. |
| 2007/0225478 A1 | 9/2007 | Querci et al. |
| 2010/0041930 A1 | 2/2010 | Gartside et al. |
| 2010/0234542 A1 | 9/2010 | Blackborow et al. |
| 2010/0286458 A1 | 11/2010 | Iselborn et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0016172 A1 | 1/2012 | Miyazoe et al. |
| 2012/0108864 A1 | 5/2012 | Gartside et al. |
| 2012/0264990 A1 | 10/2012 | Nicholas et al. |
| 2012/0283090 A1 | 11/2012 | Popp et al. |
| 2012/0289617 A1 | 11/2012 | Wang et al. |
| 2013/0058861 A1 | 3/2013 | Idem et al. |
| 2013/0085311 A1 | 4/2013 | Youn et al. |
| 2015/0141721 A1 | 5/2015 | Choi et al. |
| 2016/0237006 A1 | 8/2016 | Stoyanova et al. |
| 2017/0001925 A1 | 1/2017 | Abudawoud et al. |
| 2017/0001926 A1 | 1/2017 | Shaikh et al. |
| 2018/0057425 A1 | 3/2018 | Shaikh et al. |
| 2018/0104671 A1 | 4/2018 | Sae-Khow et al. |
| 2018/0208526 A1 | 7/2018 | Alshafei et al. |
| 2019/0169093 A1 | 6/2019 | Stoyanova et al. |
| 2020/0246864 A1 * | 8/2020 | Nishida ............... B22F 9/04 |

FOREIGN PATENT DOCUMENTS

| | | | |
|---|---|---|---|
| CN | 102325742 A | 1/2012 | |
| CN | 104370676 A | 2/2015 | |
| CN | 103772115 B | 8/2015 | |
| CN | 108043403 A | 5/2018 | |
| DE | 10013253 A1 | 9/2001 | |
| EP | 0251351 A2 | 7/1988 | |
| EP | 304515 B1 | 12/1991 | |
| EP | 2236204 A1 | 6/2010 | |
| TW | 201707789 A * | 3/2017 | ............. B01J 21/04 |
| WO | 9929805 A1 | 6/1999 | |
| WO | 2006089957 A1 | 8/2006 | |
| WO | 2009117128 A1 | 9/2009 | |
| WO | 2009126769 A2 | 10/2009 | |
| WO | 2010019595 A2 | 2/2010 | |
| WO | 2011136983 A1 | 11/2011 | |
| WO | 2015055594 A1 | 4/2015 | |
| WO | 2017003812 A1 | 1/2017 | |
| WO | 2017003817 A1 | 1/2017 | |
| WO | 2017003821 A1 | 1/2017 | |
| WO | 2019001710 A1 | 1/2019 | |

OTHER PUBLICATIONS

Alfaro et al., MgO nanoparticles coated with polyethylene glycol as carrier for 2-methoxyestradiol anticancer drug, PLoS One 148: e0214900, publication date Aug. 15, 2019.*
U.S. Notice of Allowance and Fee(s) Due dated Jan. 5, 2022 pertaining to U.S. Appl. No. 16/701,829, filed Dec. 3, 2019, 8 pages.
Eubank, William R, "Calcination Studies of Magnesium Oxides" Journal of the American Ceramic Society, vol. 34, No. 8, Aug. 1, 1951, pp. 225-229.
U.S. Office Action dated Sep. 13, 2021 pertaining to U.S. Appl. No. 16/701,829, filed Dec. 3, 2019, 31 pages.
Duong, T. H. Y. et al., "Synthesis of Magnesium Oxide Nanoplates and Their Application in Nitrogen Dioxide and Sulfur Dioxide Adsorption" Journal of Chemistry, vol. 2019, Article ID 4376429, 9 pages.
International Search Report and Written Opinion dated Feb. 19, 2021 pertaining to International application No. PCT/US2020/058829, 14 pgs.
Hai, C. et al. "Roles of ethylene glycol solvent and polymers in preparing uniformly distributed MgO nanoparticles", Journal of Asian Ceramic Societies, [Online] vol. 5, No. 2, Jun. 1, 2017, pp. 176-182.
Banks et al. "New Developments and Concepts in Enhancing Activities of Heterogeneous Metathesis Catalysts" Journal of Molecular Catalysis, 28, (1985) 117-131, 15 pgs.
Gao et al. "Controlled synthesis of MgO with diverse basic sites and its CO2 capture mechanism under different adsorption conditions" Chemical Engineering Journal 336 (2018) 710-720, 11 pgs.
Mol "Industrial applications of olefin metathesis" Journal of Molecular Catalysis A: Chemical 213 (2004) 39-45, 8 pgs.
Pilarska et al. "Recent development in the synthesis, modification and application of Mg(OH)2 and MgO: A review" Powder Technology 319 (2017) 373-407, 36 pgs.
Zhao et al. "Solvo- or hydrothermal fabrication and excellent carbon dioxide adsorption behaviors of magnesium oxides with multiple morphologies and porous structures" Materials Chemistry and Physics 128 (2011) 348-356, 9 pgs.
Zhao et al. "Mesoporous MgO promoted with NaNO3/NaNO2 for rapid and high-capacity CO2 capture at moderate temperatures" Chemical Engineering Journal 332 (2018) 216-226, 11 pgs.
Examination Report pertaining to GCC Application No. 2016/31672 dated Sep. 13, 2018.
Wu et al., "Investigation on acidity of zeolites bound with silica and alumina", Studies in Surface Science and Catalysis, 143, pp. 217-225, 2002.

(56) References Cited

OTHER PUBLICATIONS

Korean Office Action pertaining to Korea Application No. 10-2018-7003238 dated May 14, 2018 (English Translation).
Shaikh et al., "Self-Methathesis of Butenes to Propylene", Catalysis in Petroleum Refining & Petrochemicals, pp. 1-6, Dec. 7-8, 2015.
Debecker et al., "Preparation of Mo03/si02—Al203 methathesis catalysts via wet impregnation with different Mo precursors". Journal of Molecular Catalysis A: Chemical . 340, pp. 65-76, 2011.
Puriwat et al. "Elucidation of the basicity dependence of 1-butene isomerization on MgO/Mg(OH)s catalysts", Catalysis Communications, 2010, pp. 80-85.
Arudra et al., "Silicalite-1 as Efficient Catalyst for Production of Propene from 1-Butene", ACS Catalysis, 2014, 4205-4212, 4, American Chemical Society.
Awayssa et al., "Modified HZSM-5 as FCC Additive for Enhancing Light Olefins Yield from Catalytic Cracking of VGO", Applied Catalysis A: General, 2014, 172-183, 477.
Balcar, et al., "Mesoporous molecular sieves as advanced supports for olefin metathesis catalysts", Coordination Chemistry Reviews 257, 2013, pp. 3107-3124, Czech Republic.
Barrett et al., "The Determination of Pore Volume and Area Distributions in Porous Substances. I. Computations from Nitrogen Isotherms", J. Am. Chem. Soc., 1951 , 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.
Daniell et al., Enhanced Surface Acidity in Mixed Alumina-Silicas: A Low-Temperature FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.
International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.

Kumar et al., "Performance of Nano Crystalline H-ZSM-5 As Additive in FCC Catalyst: A Review", International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2C12(CHCMe3)(OR2) and W(OAr)2Cl(CHCMe3)(CH2CMe3)(OR2)", Journal of Molecular Catalysis, 1986, 36, 13-29.
Ruihua Gao, et al., "High-activity, single-site mesoporous WO3—MCF materials for the catalytic epoxidation of cycloocta-1,5-diene with aqueous hydrogen peroxide", Journal of Catalysis, 256, 2008, pp. 259-267, China.
Wang et al., "Synthesis and Structure of Silicalite-1/SBA-15 Composites Prepared by Carbon Templating and Crystallization", Journal of Materials Chemistry, 2007,4265-4273, 17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018—PCT/US2016/039012.
International Preliminary Report on Patentability dated Jan. 2, 2018—PCT/US2016/039012.
Non-Final Office Action pertaing to U.S. Appl. No. 15/398,196 dated Jan. 9, 2018.
International Search Report and Written opinion dated Mar. 28, 2018, pertaining to International Application No. 30 PCT/US2018/013945, filed Jan. 17, 2018, 9 pages.
U.S. Office Action dated Apr. 20, 2018 pertaining to Continuation U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
Office Action pertaining to U.S. Appl. No. 15/866,800 dated Jun. 29, 2018.
Office Action pertaining to U.S. Appl. No. 15/190,981 dated Apr. 4, 2017.
Office Action pertaining to U.S. Appl. No. 15/866,772 dated Aug. 28, 2018.
Harmse et al., "On the Product Formation in 1-Butene Methathesis over Supported Tungsten Catalysts", Catal. Lett, vol. 137, pp. 123-131, Apr. 2010.
International Search Report and Written Opinion dated Aug. 7, 2020 pertaining to International application No. PCT/US2020/032805 filed May 14, 2020, 15 pgs.

\* cited by examiner

METHODS OF PRODUCING ISOMERIZATION CATALYSTS

BACKGROUND

Field

The present disclosure generally relates to catalyst compositions and, more specifically, to isomerization catalysts, methods of making the isomerization catalysts, and methods of using the isomerization catalyst in the production of olefins.

Technical Background

In recent years, there has been a dramatic increase in the demand for propene to feed the growing markets for polypropylene, propylene oxide, and acrylic acid. Currently, most of the propene produced worldwide (approximately 74 million tons/year) is produced as a by-product from steam cracking units (57%), which primarily produce ethylene, or as a by-product from Fluid Catalytic Cracking (FCC) units (30%), which primarily produce gasoline. These processes cannot respond adequately to the rapid increase in propene demand. As a result, alternative methods to directly produce propene have been developed and, in particular, methods of producing propene from butene-containing feedstocks.

The production of propene from butene-containing feedstocks can be accomplished through the metathesis of the butene to propene and other olefin compounds. Metathesis of butene to produce propene can better meet the growing demand for propene. Some metathesis processes to produce propene from butene-containing feedstocks include an isomerization reaction step to increase the overall yield and propene selectivity of the metathesis process. Isomerization can be accomplished by contacting butene in the butene-containing feedstock with an isomerization catalyst upstream of or during the metathesis. However, conventional isomerization catalysts and, as a result, conventional propene production processes are inefficient, often failing to convert almost 25% of butenes and only resulting in a comparatively small propene yield.

SUMMARY

Accordingly, there is an ongoing need for improved isomerization catalysts with increased catalytic activity that, as a result, increase the conversion rate of butenes and the yield of propene from butene metathesis processes. The present disclosure is directed to methods of producing an isomerization catalyst through the hydrothermal synthesis of magnesium oxide. The present disclosure is also directed to methods of producing propene from a butene-containing feedstock through isomerization with the isomerization catalyst of the present disclosure and metathesis of butene to produce propene. The isomerization catalyst produced by the methods of the present disclosure may have increased thermal stability, which may result in a reduced deactivation rate of the isomerization catalyst when utilized at temperatures sufficient to produce propene from the isomerization and metathesis of butenes. Accordingly, the methods of the producing propene of the present disclosure may have increased efficiency, an increased conversion rate of butenes, and greater selectivity to and yield of propene.

According to one or more embodiments of the present disclosure, a method of producing an isomerization catalyst may comprise preparing a catalyst precursor solution comprising at least a magnesium precursor, a hydrolyzing agent, and polyethylene glycol. Additionally, the method may further comprise hydrothermally treating the catalyst precursor solution to produce a magnesium oxide precipitant. The method may further comprise calcining the magnesium oxide precipitant to produce the isomerization catalyst.

According to one or more other embodiments of the present disclosure, a method of producing propene from a butene-containing feedstock may comprise contacting the butene-containing feedstock with an isomerization catalyst to form an isomerization reaction effluent and contacting the isomerization reaction effluent with a metathesis catalyst to produce propene. The metathesis catalyst may be disposed in a metathesis reaction zone downstream of the isomerization catalyst. The isomerization catalyst may be prepared by a method comprising preparing a catalyst precursor solution comprising at least a magnesium precursor, a hydrolyzing agent, and polyethylene glycol, treating the catalyst precursor solution to produce a magnesium oxide precipitant, and calcining the magnesium oxide precipitant to produce the isomerization catalyst.

Additional features and advantages of the technology described in the present disclosure will be set forth in the detailed description that follows and, in part, will be readily apparent to those skilled in the art from the description or recognized by practicing the technology as described in this disclosure.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
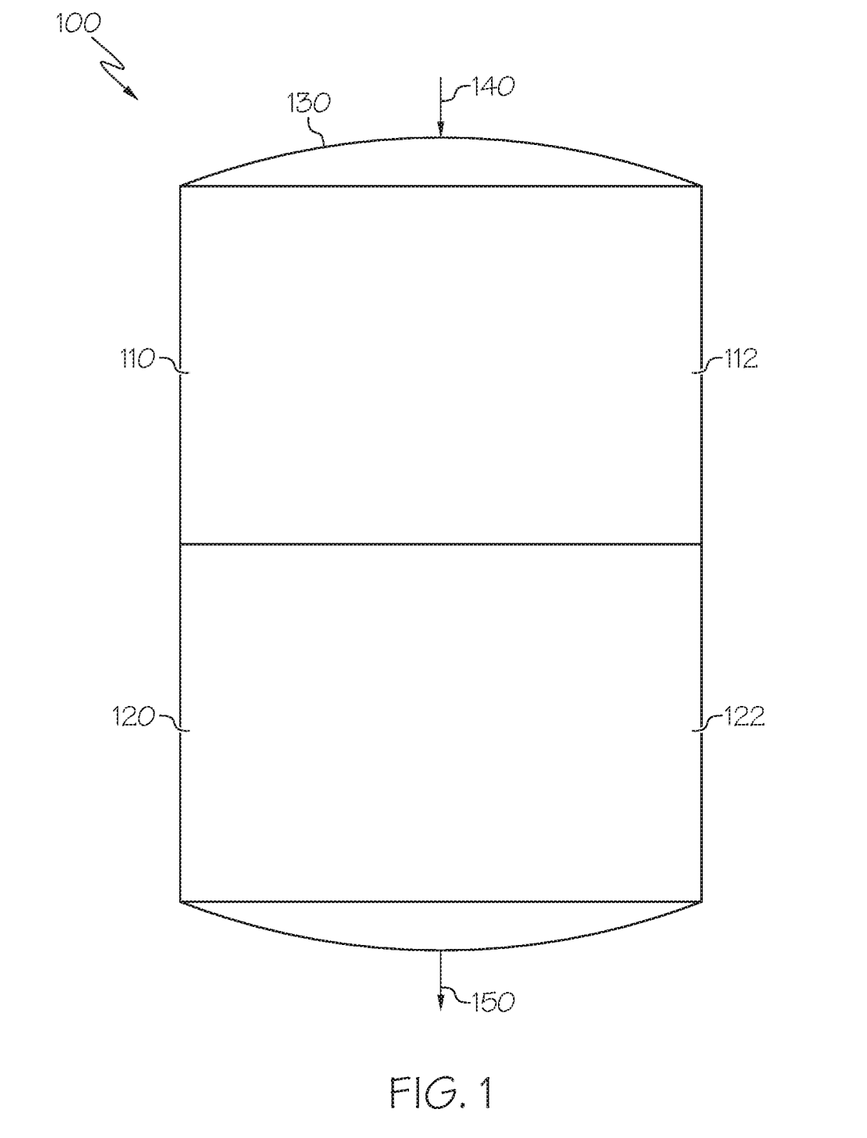
FIG. 1 schematically depicts a fixed bed continuous flow reactor including an isomerization reaction zone and a metathesis reaction zone, according to one or more embodiments of the present disclosure.
Figure 2:
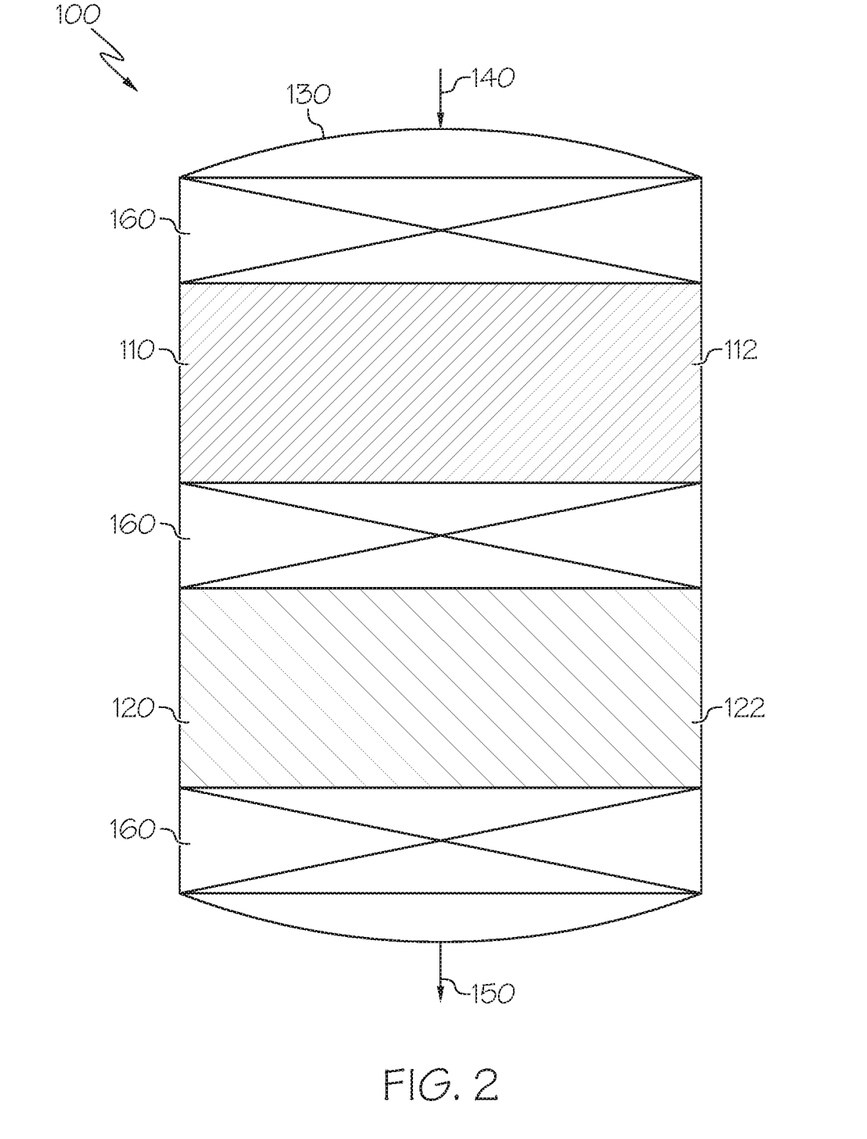
FIG. 2 schematically depicts another fixed bed continuous flow reactor including an isomerization reaction zone and a metathesis reaction zone, according to one or more embodiments of the present disclosure.

For the purpose of describing the simplified schematic illustrations and descriptions of FIGS. 1 and 2, the numerous valves, temperature sensors, electronic controllers, and the like that may be employed and well-known to a person of ordinary skill in the art are not included. Further, accompanying components that are often included in typical chemical processing operations, carrier gas supply systems, pumps, compressors, furnaces, or other subsystems are not depicted. It should be understood that these components are within the spirit and scope of the present embodiments disclosed. However, operational components, such as those described in the present disclosure, may be added to the embodiments described in the present disclosure.

Arrows in the drawings refer to process streams. However, the arrows may equivalently refer to transfer lines, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows that do not connect two or more system components may signify a product stream that exits the depicted system or a system inlet stream that enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

Reference will now be made in greater detail to various embodiments, some embodiments of which are illustrated in the accompanying drawings.

DETAILED DESCRIPTION

The present disclosure is directed to an isomerization catalyst and methods of producing the isomerization catalyst. In particular, the present disclosure is directed to methods of producing an isomerization catalyst through the hydrothermal synthesis of magnesium oxide. The present disclosure is also directed to methods of producing propene from a butene-containing feedstock through isomerization with the isomerization catalyst of the present disclosure and metathesis. In particular, the present disclosure is directed to methods of producing propene from a butene-containing feedstock that include contacting the butene-containing feedstock with the isomerization catalyst made by the synthesis methods of the present disclosure to produce an isomerization reaction effluent and contacting the isomerization reaction effluent with a metathesis catalyst to produce a metathesis effluent that includes at least propene. The isomerization catalyst produced by the methods of the present disclosure may have increased thermal stability, which may result in a reduced deactivation rate of the isomerization catalyst at temperatures sufficient to produce propene from the isomerization and metathesis of butenes. Accordingly, systems incorporating the isomerization catalyst produced by the present disclosure may have increased efficiency, an increased conversion rate of butenes, and a greater yield of propene.

As used throughout the present disclosure, the term "butene" or "butenes" may refer to compositions comprising one or more than one of 1-butene, trans-2-butene, cis-2-butene, isobutene, or mixtures of these isomers. As used throughout the present disclosure, the term "normal butenes" may refer to compositions comprising one or more than one of 1-butene, trans-2-butene, cis-2-butene, or mixtures of these isomers, and are substantially free of isobutene. As used in the present disclosure, the term "2-butene" may refer to trans-2-butene, cis-2-butene, or a mixture of these two isomers. As used in the present disclosure, the term "substantially free" of a component means less than 1 wt. % of that component in a particular portion of a catalyst, stream, or reaction zone. For example, a composition, which may be substantially free of isobutene, may comprise less than 1 wt. % of isobutene.

As shown in Reaction 1 (RXN 1), the isomerization of 2-butene to 1-butene, and the isomerization of 1-butene to 2-butene, is an equilibrium reaction, as denoted by the bi-directional arrows with single heads. The isomerization of 2-butene and 1-butene may be achieved with an isomerization catalyst. As used in the present disclosure, the term "isomerization catalyst" may refer to a catalyst that promotes isomerization of alkenes, including, for example, isomerization of 2-butenes to 1-butene. As shown in Reaction 2 (RXN 2), the cross-metathesis of 1-butene and 2-butene may produce 1-propene and 2-pentene. As used in the present disclosure, the term "cross-metathesis" may refer to an organic reaction that involves the redistribution of fragments of alkenes by the scission and regeneration of carbon-carbon double bonds. In the case of metathesis between 2-butene and 1-butene, the redistribution of these carbon-carbon double bonds through metathesis produces propene and $C_5$-$C_6$ olefins. The cross-metathesis of 1-butene and 2-butene may be achieved with a metathesis catalyst. As used in the present disclosure, the term "metathesis catalyst" may refer to a catalyst that promotes the metathesis reaction of alkenes to form other alkenes. The metathesis catalyst may also isomerize 2-butenes to 1-butene through a "self-metathesis" reaction mechanism.

Referring to RXN 1 and RXN 2, the isomerization and metathesis reactions are not limited to these reactants and products; however, RXN 1 and RXN 2 provide a simplified illustration of the reaction methodology. As shown in RXN 2, metathesis reactions may take place between two alkenes. The groups bonded to the carbon atoms of the carbon-carbon double bond may be exchanged between the molecules to produce two new alkenes with the exchanged groups. The specific metathesis catalyst that is selected may generally determine whether a cis-isomer or trans-isomer is formed, as the formation of a cis-isomer or a trans-isomer may be, at least partially, a function of the coordination of the alkenes with the catalyst.

In operation, a product stream comprising propene may be produced from a feedstock containing butene through isomerization and metathesis by contacting the feedstock with an isomerization catalyst and a metathesis catalyst. Optionally, the metathesis reaction effluent, which may comprise $C_5$-$C_6$ olefins, may be contacted with a cracking catalyst to further increase the yield of propene through the cracking of the $C_5$-$C_6$ olefins. The feedstock may comprise 1-butene, trans-2-butene, cis-2-butene, or combinations of these. The feedstock may further comprise other $C_1$-$C_6$ components. The presence of isobutene and other inert gases or non-olefinic hydrocarbons, such as n-butane, in the feedstock do not negatively affect the target isomerization and metathesis reactions, and the amount of any side products formed as a result of their presence in the feedstock do not affect the overall yield of total propene.

Referring now to FIG. 1, a system for producing propene from a feedstock containing butene is depicted, the system being designated by reference number 100. The system 100 may include an isomerization reaction zone 110 and a metathesis reaction zone 120. The metathesis reaction zone 120 may be positioned downstream of the isomerization reaction zone 110. The isomerization reaction zone 110 and the metathesis reaction zone 120 may be disposed within a single reactor 130 or in multiple reactors. As depicted in FIG. 1, a feedstock 140 may be introduced into the reactor 130, and a metathesis effluent 150 may be passed out of the reactor 130. Accordingly, the feedstock 140 may be introduced into the reactor 130, passed through the isomerization reaction zone 110, passed through the metathesis reaction zone 120, and passed out of the reactor 130 as the metathesis effluent 150.

As described previously in the present disclosure, the feedstock 140 may comprise 1-butene, cis-2-butene, trans-2-butene, or combinations of these. The feedstock 140 may comprise from 10 wt. % to 100 wt. % 1-butene based on the total weight of the feedstock 140. For example, the feedstock 140 may comprise from 10 wt. % to 80 wt. %, from 10 wt. % to 60 wt. %, from 10 wt. % to 40 wt. %, from 10 wt. % to 20 wt. %, from 20 wt. % to 100 wt. %, from 20 wt. % to 80 wt. %, from 20 wt. % to 60 wt. %, from 20 wt. % to 40 wt. %, from 40 wt. % to 100 wt. %, from 40 wt. % to 80 wt. %, from 40 wt. % to 60 wt. %, from 60 wt. % to 100 wt. %, from 60 wt. % to 80 wt. %, or from 80 wt. % to 100 wt. % 1-butene based on the total weight of the feedstock 140. The feedstock 140 may comprise from 10 wt. % to 100 wt. % 2-butene (that is, cis-2-butene, trans-2-butene, or both) based on the total weight of the feedstock 140. For example, the feedstock 140 may comprise from 10 wt. % to 80 wt. %, from 10 wt. % to 60 wt. %, from 10 wt. % to 40 wt. %, from 10 wt. % to 20 wt. %, from 20 wt. % to 100 wt. %, from 20 wt. % to 80 wt. %, from 20 wt. % to 60 wt. %, from 20 wt. % to 40 wt. %, from 40 wt. % to 100 wt. %, from 40 wt. % to 80 wt. %, from 40 wt. % to 60 wt. %, from 60 wt. % to 100 wt. %, from 60 wt. % to 80 wt. %, or from 80 wt. % to 100 wt. % 2-butene based on the total weight of the feedstock 140. Additionally, the feedstock 140 may be substantially free of ethylene. For example, the feedstock 140, which may be substantially free of ethylene, may comprise less than 1 wt. % of ethylene.

The feedstock 140 may comprise a raffinate stream. As used in the present disclosure, the term "raffinate" may refer to the residue $C_4$ stream from a naphtha cracking process or from a gas cracking process when components are removed (the $C_4$ stream typically containing, as its primary components, n-butane, 1-butene, 2-butene, isobutene, and 1,3-butadiene, and optionally some isobutane and said chief components together forming up to 99% or more of the $C_4$ stream). The feedstock 140 may comprise a raffinate-1 stream. As used in the present disclosure, the term "raffinate-1" may refer to the $C_4$ residual obtained after separation of 1,3-butadiene from a raffinate stream, and comprises mainly 2-butene, 1-butene, and isobutene, which may make up greater than or equal to 55 wt. % of the raffinate-1 stream. For example, the raffinate-1 stream may comprise from 10 wt. % to 30 wt. % of 2-butene, from 25 wt. % to 50 wt. % of 1-butene, and from 20 wt. % to 50 wt. % isobutene, based on the total weight of the raffinate-1 stream. The feedstock 140 may comprise a raffinate-2 stream. As used in the present disclosure, the term "raffinate-2" may refer to the $C_4$ residual obtained after separation of 1,3-butadiene and isobutene from a raffinate stream, and comprises mainly 2-butene, 1-butene, and n-butane, which may make up greater than or equal to 45 wt. % of the raffinate-2 stream. For example, the raffinate-2 stream may comprise from 20 wt. % to 60 wt. % of 2-butene, from 10 wt. % to 60 wt. % of 1-butene, and from 15 wt. % to 25 wt. % n-butane, based on the total weight of the raffinate-2 stream. The feedstock 140 may comprise a raffinate-3 stream. As used in the present disclosure, the term "raffinate-3" may refer to the $C_4$ residual obtained after separation of 1,3-butadiene, isobutene, and 1-butene from the $C_4$ raffinate stream, and comprises mainly 2-butene, n-butane, and unseparated 1-butene, which may make up greater than or equal to 40 wt. % of the raffinate-3 stream. For example, the raffinate-3 stream may comprise from 30 wt. % to 70 wt. % of 2-butene and from 10 wt. % to 30 wt. % of n-butane, based on the total weight of the raffinate-3 stream.

While the isomerization reaction zone 110 and the metathesis reaction zone 120 are depicted in FIG. 1 as being in a single reactor, it should be understood that each reaction zone (that is, the isomerization reaction zone 110 and the metathesis reaction zone 120) may be disposed in separate reactors, arranged in series. Accordingly, the two reactors may be arranged in series, such that the feedstock 140 may be introduced into a first reactor comprising the isomerization reaction zone 110, and the resulting isomerization effluent may be passed to a second reactor comprising the metathesis reaction zone 120 to produce the metathesis effluent 150. Multiple reactors in series may enable each of the isomerization reaction zone 110 and the metathesis reaction zone 120 to be operated at different operating conditions. For example, the first reactor comprising the isomerization reaction zone 110 may be operated at an isomerization reaction temperature, and the second reactor comprising the metathesis reaction zone 120 may be operated at a metathesis reaction temperature different from the isomerization temperature. The isomerization reaction temperature may be less than the metathesis reaction temperature.

The isomerization reaction zone 110 may be maintained at an isomerization reaction temperature sufficient to promote equilibration of the isomerization reactions between 2-butene and 1-butene in the feedstock 140. The isomerization reaction temperature may be from 100 degrees Celsius (° C.) to 600° C. For example, the isomerization reaction temperature may be from 100° C. to 550° C., from 100° C. to 450° C., from 100° C. to 400° C., from 100° C. to 300° C., from 100° C. to 250° C., from 100° C. to 150° C., from 150° C. to 600° C., from 150° C. to 550° C., from 150° C. to 450° C., from 150° C. to 400° C., from 150° C. to 300° C., from 150° C. to 250° C., from 250° C. to 600° C., from 250° C. to 550° C., from 250° C. to 450° C., from 250° C. to 400° C., from 250° C. to 300° C., from 300° C. to 600° C., from 300° C. to 550° C., from 300° C. to 450° C., from 300° C. to 400° C., from 400° C. to 600° C., from 400° C. to 550° C., from 400° C. to 450° C., from 450° C. to 600° C., from 450° C. to 550° C., or from 550° C. to 600° C. These temperature ranges sufficient to promote equilibration of the isomerization reactions may allow the operating temperature of the entire system 100 to be decreased in comparison to systems that do no comprise an isomerization reaction zone. Systems that do not comprise an isomerization reaction zone rely upon the metathesis catalyst to self-metathesize the 2-butene to 1-butene, or to self-metathesize the 1-butene to 2-butene. Without being bound by any particular theory, it is believed that the isomerization reaction zone 110 is capable of promoting equilibration of the isomerization reactions at a lower temperature than a temperature required by the metathesis catalyst to promote self-metathesis. These lower temperatures may lead to an increase in propene yield. These lower temperatures may also provide the immediate benefit of lower operating costs due to the reduced heating requirements.

The metathesis reaction zone 120 may be maintained at a metathesis reaction temperature sufficient to promote the cross-metathesis reaction of 2-butene and 1-butene. The metathesis reaction temperature may be from 100 degrees Celsius (° C.) to 600° C. For example, the metathesis reaction temperature may be from 100° C. to 550° C., from 100° C. to 450° C., from 100° C. to 400° C., from 100° C. to 300° C., from 100° C. to 250° C., from 100° C. to 150° C., from 150° C. to 600° C., from 150° C. to 550° C., from 150° C. to 450° C., from 150° C. to 400° C., from 150° C. to 300° C., from 150° C. to 250° C., from 250° C. to 600° C., from 250° C. to 550° C., from 250° C. to 450° C., from 250° C. to 400° C., from 250° C. to 300° C., from 300° C. to 600° C., from 300° C. to 550° C., from 300° C. to 450° C., from 300° C. to 400° C., from 400° C. to 600° C., from 400° C. to 550° C., from 400° C. to 450° C., from 450° C. to 600° C., from 450° C. to 550° C., or from 550° C. to 600° C. These temperature ranges sufficient to promote the cross-metathesis reactions may allow the operating temperature of the entire system 100 to be decreased in comparison to systems that do not include an isomerization reaction zone. As described previously in the present disclosure, systems that do no include an isomerization reaction zone rely upon the metathesis catalyst to self-metathesize the 2-butene to 1-butene, or to self-metathesize the 1-butene to 2-butene. Without being bound by any particular theory, it is believed that the metathesis reaction zone may not be capable of promoting self-metathesis at a rate sufficient to produce the necessary amounts of either 1-butene or 2-butene. Accordingly, these lower temperatures may reduce the yield of propene in systems that do not include an isomerization reaction zone. These lower temperatures may also provide the immediate benefit of lower operating costs due to the reduced heating requirements.

Referring still to FIG. 1, the isomerization reaction zone 110 of the system 100 may include an isomerization catalyst 112. The isomerization catalyst 112 may be a magnesium oxide (MgO) catalyst. The magnesium oxide catalyst may promote equilibration of the isomerization reactions of 2-butene and 1-butene in the feedstock 140 to 1-butene and 2-butene, respectively. For example, when the feedstock 140 has a greater concentration of 2-butene compared to 1-butene, the magnesium oxide catalyst may isomerize at least a portion of the 2-butene to 1-butene. Conversely, when the feedstock 140 has a greater concentration of 1-butene compared to 2-butene, the magnesium oxide catalyst may isomerize at least a portion of the 1-butene to 2-butene. The isomerization reaction zone 110 may produce an isomerization effluent that may comprise 1-butene, cis-2-butene, trans-2-butene, or combinations of these. The magnesium oxide catalyst may also reduce the production of isobutene and other undesirable side-products in the metathesis reaction zone 120. Without being bound by any particular theory, it is believed that the promotion of equilibration of the isomerization reaction between 2-butene and 1-butene in the feedstock 140 by the magnesium oxide catalyst may maintain proportions of 1-butene and 2-butene in the metathesis reaction zone 120 such that the butenes are consumed primarily in the cross-metathesis reaction rather than undergoing side reactions, such as those side reactions that produce isobutene. Reducing the amounts of unreacted butene may also reduce the amount of isobutene.

The magnesium oxide catalyst may also be used to remove contaminants from the feedstock 140. Metathesis catalysts may be sensitive to poisons, such as peroxides, water, carbon dioxide, oxygenates, heavy metals, nitrogen compounds, and sulfur compounds, which may have a deleterious effect on the performance of the metathesis catalyst. The magnesium oxide catalyst is capable of removing some poisons, such as peroxides, for example, that may be present in the feedstock 140 in low concentrations. Accordingly, the magnesium oxide catalyst may be used as a guard-bed for the metathesis catalyst by removing or destroying traces of contaminants or poisons that may be present in the feedstock 140. When functioning as a guard bed, the magnesium oxide catalyst may reduce fouling of the metathesis catalyst activity, which may result in improved yield of propene and longer service life of the metathesis catalyst in the metathesis reaction zone. The magnesium oxide catalyst may further enhance conversion of butene to propene through generations of gas-phase "excited species," such as allyl or allyl-oxo radicals, for example, which may be initiators or precursors of metathesis sites. By generating initiators or precursors of metathesis sites, the magnesium oxide catalyst may further enhance the metathesis activities of the metathesis reaction zone.

As described previously in the present disclosure, commercially-available magnesium oxide catalysts may have poor catalytic activity, inferior thermal stability, or both, which results in a decreased yield of propene. Accordingly, the isomerization catalyst of the present disclosure may be prepared using a hydrothermal synthesis method. The resulting isomerization catalyst may have increased thermal stability and catalytic activity compared to commercially-available magnesium oxide catalysts. During hydrothermal synthesis, the isomerization catalyst may be synthesized from the reaction of a magnesium precursor, such as but not limited to magnesium nitrate hexahydrate, and a hydrolyzing agent, such as but not limited to urea, in an aqueous solution. The aqueous solution may then be hydrothermally treated in order to produce a magnesium oxide precipitant. The magnesium oxide resulting from the reaction taking place during the hydrothermal treatment may precipitate out of the aqueous solution as a white solid, which may then be separated, washed, dried, and calcined. The isomerization catalyst may also be prepared using a surfactant-assisted hydrothermal synthesis method, in which the aqueous solution further comprises a surfactant, such as polyethylene glycol (PEG), in an aqueous solution. The inclusion of a surfactant may increase the surface area and cumulative volume of pores, and reduce the average particle size of the resulting magnesium oxide.

As described previously in the present disclosure, the aqueous solution used in the hydrothermal synthesis may comprise a magnesium precursor and a hydrolyzing agent. The magnesium precursor may be selected from one or more of magnesium nitrate hexahydrate, magnesium acetate tetrahydrate, and magnesium chloride tetrahydrate. The hydrolyzing agent may be selected from one or more of urea, a diamine, such as ethylene diamine, and ammonium hydroxide. The aqueous solution used in the hydrothermal synthesis may comprise the magnesium precursor and the hydrolyzing agent in a molar ratio of from 1:10 to 1:1. For example, the aqueous solution used in the hydrothermal synthesis may comprise the magnesium precursor and the hydrolyzing agent in a molar ratio of from 1:10 to 1:2, from 1:10 to 1:3, from 1:10 to 1:4, from 1:10 to 1:5, from 1:10 to 1:6, from 1:10 to 1:7, from 1:10 to 1:8, from 1:10 to 1:9, from 1:9 to 1:1, from 1:9 to 1:2, from 1:9 to 1:3, from 1:9 to 1:4, from 1:9 to 1:5, from 1:9 to 1:6, from 1:9 to 1:7, from 1:9 to 1:8, from 1:8 to 1:1, from 1:8 to 1:2, from 1:8 to 1:3, from 1:8 to 1:4, from 1:8 to 1:5, from 1:8 to 1:6, from 1:8 to 1:7, from 1:7 to 1:1, from 1:7 to 1:2, from 1:7 to 1:3, from 1:7 to 1:4, from 1:7 to 1:5, from 1:7 to 1:6, from 1:6 to 1:1, 1:6 to 1:2, from 1:6 to 1:3, from 1:6 to 1:4, from 1:6 to 1:5, from 1:5 to 1:1, from 1:5 to 1:2, from 1:5 to 1:3, from 1:5 to 1:4, from 1:4 to 1:1, from 1:4 to 1:2, from 1:4 to 1:3, from 1:3 to 1:1, from 1:3 to 1:2, or from 1:2 to 1:1. Without being bound by any particular theory, it is believed that the hydrolyzing agent may increase the yield of magnesium oxide during the hydrothermal synthesis by improving the seeding effect and crystallization of magnesium oxide during precipitation. For example, when the aqueous solution used in the hydrothermal synthesis comprises the magnesium precursor and the hydrolyzing agent in a molar ratio less than 1:10, the yield of the magnesium oxide, and the isomerization catalyst, may be reduced. This reduced yield may render the process unsuitable for the production of the isomerization catalyst on an industrial scale.

As described previously in the present disclosure, the aqueous solution used in the hydrothermal synthesis may further comprise polyethylene glycol. The aqueous solution used in the hydrothermal synthesis may comprise the magnesium precursor and polyethylene glycol in a molar ratio of from 1:0.1 to 1:0.01. For example, the aqueous solution used in the hydrothermal synthesis may comprise the magnesium precursor and polyethylene glycol in a molar ratio of from 1:0.1 to 1:0.02, from 1:0.1 to 1:0.03, from 1:0.1 to 1:0.04, from 1:0.1 to 1:0.05, from 1:0.1 to 1:0.06, from 1:0.1 to 1:0.07, from 1:0.1 to 1:0.08, from 1:0.1 to 1:0.09, from 1:0.09 to 1:0.01, from 1:0.09 to 1:0.02, from 1:0.09 to 1:0.03, from 1:0.09 to 1:0.04, from 1:0.09 to 1:0.05, from 1:0.09 to 1:0.06, from 1:0.09 to 1:0.07, from 1:0.09 to 1:0.08, from 1:0.08 to 1:0.01, from 1:0.08 to 1:0.02, from 1:0.08 to 1:0.03, from 1:0.08 to 1:0.04, from 1:0.08 to 1:0.05, from 1:0.08 to 1:0.06, from 1:0.08 to 1:0.07, from 1:0.07 to 1:0.01, from 1:0.07 to 1:0.02, from 1:0.07 to 1:0.03, from 1:0.07 to 1:0.04, from 1:0.07 to 1:0.05, from 1:0.07 to 1:0.06, from 1:0.06 to 1:0.01, 1:0.06 to 1:0.02, from 1:0.06 to 1:0.03, from 1:0.06 to 1:0.04, from 1:0.06 to 1:0.05, from 1:0.05 to 1:0.01, from 1:0.05 to 1:0.02, from 1:0.05 to 1:0.03, from 1:0.05 to 1:0.04, from 1:0.04 to 1:0.01, from 1:0.04 to 1:0.02, from 1:0.04 to 1:0.03, from 1:0.03 to 1:0.01, from 1:0.03 to 1:0.02, or from 1:0.02 to 1:0.01. Without being bound by any particular theory, it is believed that polyethylene glycol may act as a surface directing agent during hydrothermal synthesis, affecting the mesoporosity of the resulting magnesium oxide and, as a result, the surface area and pore volume of the isomerization catalyst. For example, when the aqueous solution used in the hydrothermal synthesis comprises the magnesium precursor and polyethylene glycol in a molar ratio less than 1:0.1, the surface area and pore volume of the resulting isomerization catalyst may be reduced, resulting in a decrease in catalytic activity.

The pH of the aqueous solution used in the hydrothermal synthesis may be adjusted such that the aqueous solution is more acidic or more basic. The pH of the aqueous solution used in the hydrothermal synthesis may be adjusted such that the pH of the aqueous solution is from 3 to 7. For example, the pH of the aqueous solution used in the hydrothermal synthesis may be adjusted such that the pH of the aqueous solution is from 3 to 6, from 3 to 5, from 3 to 4, from 4 to 7, from 4 to 6, from 4 to 5, from 5 to 7, from 5 to 6, or from 6 to 7. In embodiments, the pH of the aqueous solution used in the hydrothermal synthesis may be adjusted such that the pH of the aqueous solution is from 8 to 12. For example, the pH of the aqueous solution used in the hydrothermal synthesis may be adjusted such that the pH of the aqueous solution is from 8 to 11, from 8 to 10, from 8 to 9, from 9 to 12, from 9 to 11, from 9 to 10, from 10 to 12, from 10 to 11, or from 11 to 12. Without being bound by any particular theory, it is believed that the pH of the aqueous solution may affect the yield of the isomerization catalyst, the morphology of the isomerization catalyst, or both. For example, acidic or basic aqueous solutions may result in the increased precipitation of magnesium oxide during hydrothermal synthesis and, as a result, increase the yield of the isomerization catalysts. Additionally, the morphology of the isomerization catalyst, which may increase or decrease the catalytic activity, may be determined by the presence of anionic and cationic species within the aqueous solution. In particular, the anionic and cationic species, the concentration of which increases with the acidity or basicity of the aqueous solution, may be responsible for stearic hindrance during hydrothermal synthesis. Such stearic hindrance may affect the morphology of the resulting magnesium oxide and, as a result, increases the catalytic activity of the isomerization catalyst.

As described previously in the present disclosure, the aqueous solution may be hydrothermally treated in order to produce a magnesium oxide precipitant. The hydrothermal treatment may comprise the heating of the aqueous solution. The heating of the aqueous solution may be conducted in a pressure vessel, such as an autoclave. The hydrothermal treatment of the aqueous solution may comprise heating the aqueous solution to a temperature sufficient to cause the reaction of the magnesium precursor and the hydrolyzing agent, resulting in the precipitation of magnesium oxide from the aqueous solution. The hydrothermal treatment of the aqueous solution may comprise heating the aqueous solution to a temperature of from 100° C. to 140° C. For example, the hydrothermal treatment of the aqueous solution may comprise heating the aqueous solution to a temperature of from 100° C. to 135° C., from 100° C. to 130° C., from 100° C. to 125° C., from 100° C. to 120° C., from 100° C. to 115° C., from 100° C. to 110° C., from 100° C. to 105° C., from 105° C. to 140° C., from 105° C. to 135° C., from 105° C. to 130° C., from 105° C. to 125° C., from 105° C. to 120° C., from 105° C. to 115° C., from 105° C. to 110° C., from 110° C. to 140° C., from 110° C. to 135° C., from 110° C. to 130° C., from 110° C. to 125° C., from 110° C. to 120° C., from 110° C. to 115° C., from 115° C. to 140°

C., from 115° C. to 135° C., from 115° C. to 130° C., from 115° C. to 125° C., from 115° C. to 120° C., from 120° C. to 140° C., from 120° C. to 135° C., from 120° C. to 130° C., from 120° C. to 125° C., from 125° C. to 140° C., from 125° C. to 135° C., from 125° C. to 130° C., from 130° C. to 140° C., from 130° C. to 135° C., or from 135° C. to 140° C.

The hydrothermal treatment of the aqueous solution may comprise heating the aqueous solution for an amount of time sufficient to cause the reaction of the magnesium precursor and the hydrolyzing agent, resulting in the precipitation of magnesium oxide from the aqueous solution. In embodiments, the hydrothermal treatment of the aqueous solution may comprise heating the aqueous solution for a duration of from 48 hours to 96 hours. For example, the hydrothermal treatment of the aqueous solution may comprise heating the aqueous solution for a duration of from 48 hours to 84 hours, from 48 hours to 72 hours, from 48 hours to 60 hours, from 60 hours to 96 hours, from 60 hours to 84 hours, from 60 hours to 72 hours, from 72 hours to 96 hours, from 72 hours to 84 hours, or from 84 hours to 96 hours.

As described previously in the present disclosure, after hydrothermal treatment the precipitated magnesium oxide may be separated, washed, dried, and calcined to produce the isomerization catalyst. Without being bound by any particular theory, it is believed that the calcination of the magnesium oxide to produce the isomerization catalyst may activate the reaction sites for butene isomerization. Magnesium oxide is generally basic in nature and the basicity of the magnesium oxide may be influenced by the calcination temperature and process. Calcination conditions may influence the strength and quantity of basic reaction sites in the isomerization catalyst. Selection of the appropriate calcination temperature may enhance the number and strength of the basic sites in the magnesium oxide, thus, enhancing the isomerization performance of the isomerization catalyst. The "calcination temperature" is a target average temperature to which the magnesium oxide is heated and at which the magnesium oxide is calcined over a period of time during the calcination process. The "ramping rate," as used in the present disclosure, is a rate at which the temperature of the magnesium oxide is increased from a starting temperature to the calcination temperature. The magnesium oxide may be placed in the calcination oven and the temperature of the calcination oven may be increased at the ramping rate to the calcination temperature. Then, the magnesium oxide may be maintained at the calcination temperature for a predetermined period of time. At the end of the predetermined period of time, the calcined magnesium oxide may be allowed to slowly cool down to ambient temperature. Optionally, the isomerization catalyst may be calcined a second time. The calcination temperature, ramping rate, and duration of the second calcination process may each be the same or different from the calcination temperature, ramping rate, and duration of the first calcination process.

The magnesium oxide may be calcined in a calcination oven at a calcination temperature of from 450° C. to 650° C. For example, the magnesium oxide may be calcined in a calcination oven at a calcination temperature of from 450° C. to 600° C., from 450° C. to 550° C., from 450° C. to 500° C., from 500° C. to 650° C., from 500° C. to 600° C., from 500° C. to 550° C., from 550° C. to 650° C., from 550° C. to 600° C., or from 600° C. to 650° C. The ramping rate of the calcination process may be from 1 degree Celsius per minute (° C./min) to 4° C./min. For example, the ramping rate of the calcination process may be from 1° C./min to 3° C./min, from 1° C./min to 2.5° C./min, from 1° C./min to 2° C./min, from 1.5° C./min to 2° C./min, from 1.5° C./min to 4° C./min, from 1.5° C./min to 3° C./min, from 1.5° C./min to 2.5° C./min, from 1.5° C./min to 2° C./min, from 2° C./min to 4° C./min, from 2° C./min to 3° C./min, from 2° C./min to 2.5° C./min, from 2.5° C./min to 4° C./min, from 2.5° C./min to 3° C./min, or from 3° C./min to 4° C./min. The magnesium oxide may be calcined in the calcination oven for a duration of from 1 hour to 10 hours. For example, the magnesium oxide may be calcined in the calcination oven for a duration of from 1 hour to 8 hours, from 1 hour to 6 hours, from 1 hour to 4 hours, from 1 hour to 2 hours, from 2 hours to 10 hours, from 2 hours to 8 hours, from 2 hours to 6 hours, from 2 hours to 4 hours, from 4 hours to 10 hours, from 4 hours to 8 hours, from 4 hours to 6 hours, from 6 hours to 10 hours, from 6 hours to 8 hours, or from 8 hours.

The isomerization catalyst resulting from the process of the present disclosure may have a surface area of from 125 square meters per gram ($m^2/g$) to 225 $m^2/g$, as determined by the Brunauer Emmett-Teller (BET) method. For example, the isomerization catalyst may have a surface area of from 125 $m^2/g$ to 200 $m^2/g$, from 125 $m^2/g$ to 175 $m^2/g$, from 125 $m^2/g$ to 150 $m^2/g$, from 150 $m^2/g$ to 225 $m^2/g$, from 150 $m^2/g$ to 200 $m^2/g$, from 150 $m^2/g$ to 175 $m^2/g$, from 175 $m^2/g$ to 225 $m^2/g$, from 175 $m^2/g$ to 200 $m^2/g$, or from 200 $m^2/g$ to 225 $m^2/g$, as determined by the BET method.

The isomerization catalyst resulting from the process of the present disclosure may have a cumulative pore volume of from 0.20 cubic centimeters per gram ($cm^3/g$) to 0.35 $cm^3/g$, as determined by the Barrett, Joyner, and Halenda (BJH) method. For example, the isomerization catalyst may have a cumulative pore volume of from 0.20 $cm^3/g$ to 0.32 $cm^3/g$, from 0.20 $cm^3/g$ to 0.29 $cm^3/g$, from 0.20 $cm^3/g$ to 0.26 $cm^3/g$, from 0.20 $cm^3/g$ to 0.23 $cm^3/g$, from 0.23 $cm^3/g$ to 0.35 $cm^3/g$, from 0.23 $cm^3/g$ to 0.32 $cm^3/g$, from 0.23 $cm^3/g$ to 0.29 $cm^3/g$, from 0.23 $cm^3/g$ to 0.26 $cm^3/g$, from 0.26 $cm^3/g$ to 0.35 $cm^3/g$, from 0.26 $cm^3/g$ to 0.32 $cm^3/g$, from 0.26 $cm^3/g$ to 0.29 $cm^3/g$, from 0.29 $cm^3/g$ to 0.35 $cm^3/g$, from 0.29 $cm^3/g$ to 0.32 $cm^3/g$, or from 0.32 $cm^3/g$ to 0.35 $cm^3/g$, as determined by the BJH method.

The isomerization catalyst resulting from the process of the present disclosure may have an average pore width of from 5 nanometers (nm) to 10 nm, as determined by the BJH method. For example, the isomerization catalyst may have an average pore width of from 5 nm to 9 nm, from 5 nm to 8 nm, from 5 nm to 7 nm from 5 nm to 6 nm, from 6 nm to 10 nm, from 6 nm to 9 nm, from 6 nm to 8 nm, from 6 nm to 7 nm, from 7 nm to 10 nm, from 7 nm to 9 nm, from 7 nm to 8 nm, from 8 nm to 10 nm, from 8 nm to 9 nm, or from 9 nm to 10 nm, as determined by the BJH method.

The isomerization catalyst resulting from the process of the present disclosure may have an average particle size of from 20 nm to 50 nm, as calculated by the Scherrer equation. For example, the isomerization catalyst may have an average particle size of from 20 nm to 45 nm, from 20 nm to 40 nm, from 20 nm to 35 nm, from 20 nm to 30 nm, from 20 nm to 25 nm, from 25 nm to 50 nm, from 25 nm to 45 nm, from 25 nm to 40 nm, from 25 nm to 35 nm, from 25 nm to 30 nm, from 30 nm to 50 nm, from 30 nm to 45 nm, from 30 nm to 40 nm, from 30 nm to 35 nm, from 35 nm to 50 nm, from 35 nm to 45 nm, from 35 nm to 40 nm, from 40 nm to 50 nm, from 40 nm to 45 nm, or from 45 nm to 50 nm, as calculated by the Scherrer equation.

The isomerization catalyst having these properties (that is, the previously described surface area, cumulative pore volume, average pore width, and average particle size) may have increased catalytic activity and thermal stability compared to commercially-available magnesium oxide catalysts. As a result, the system 100 may have an increased butene conversion rate and an increased propene yield.

As described previously in the present disclosure, the feedstock 140 may be contacted with the isomerization catalyst 112 in the isomerization reaction zone 110 to produce an isomerization effluent that comprises 1-butene and 2-butene. The isomerization effluent may then be passed to the metathesis reaction zone 120, where the isomerization effluent may be contacted with the metathesis catalyst 122 to produce the metathesis effluent 150. Referring again to FIG. 1, the metathesis reaction zone 120 may include a metathesis catalyst 122. The metathesis catalyst 122 may promote the conversion of 1-butene and 2-butene in the isomerization effluent to propene and other alkenes through cross-metathesis. The metathesis catalyst 122 may comprise a metal oxide deposited on a support material. The metal oxide may comprise any metal oxide sufficient to promote the cross-metathesis of butenes at the operational conditions of the system 100, such as tungsten oxide. The support material may be a mesoporous silica support material, such as a molecular sieve or zeolite. As used in the present disclosure, the term "mesoporous" may refer to a material having an average pore size of greater than 2 nm and less than 50 nm. For example, the metathesis catalyst 122 may comprise a mesoporous silica support impregnated with tungsten oxide. The metathesis reaction zone 120 may produce a metathesis reaction effluent that may include propene and other alkanes and alkenes, such as $C_5+$ olefins, for example. The metathesis reaction effluent may also include unreacted butenes, such as 1-butene, cis-2-butene, trans-2-butene, or combinations of these.

Referring now to FIG. 2, in embodiments, a fluid/solid separator 160 may be disposed downstream of the metathesis reaction zone 120, upstream of the isomerization reaction zone 110, between the isomerization reaction zone 110 and the metathesis reaction zone 120, or combinations of these. As used in the present disclosure, the term "fluid/solid separator" may refer to a fluid permeable barrier between catalyst beds that substantially prevents solid catalyst particles in one catalyst bed from migrating to an adjacent catalyst bed, while allowing for reactants and products to move through the separator. The fluid/solid separator 160 may be chemically inert and generally makes no contribution to the reaction chemistry. Inserting the fluid/solid separator 160 between the isomerization reaction zone 110 and the metathesis reaction zone 120 may maintain the isomerization catalyst 112 and the metathesis catalyst 122 in the isomerization reaction zone 110 and the metathesis reactions zone 120, respectively, and prevent migration of different catalysts between reaction zones, which may lead to increased production of undesired by-products and decreased yield.

The isomerization reaction zone 110 and the metathesis reaction zone 120 may have a relatively small amount of the different type of catalyst from one reaction zone, or may be completely free of catalyst from the other reaction zone. For example, the isomerization reaction zone 110 may comprise less than 10 wt. % of the metathesis catalyst 122 from the metathesis reaction zone 120. Similarly, the metathesis reaction zone 120 may comprise less than 10 wt. % of the isomerization catalyst 112 from the isomerization reaction zone 110. In embodiments, the isomerization reaction zone 110 and the metathesis reaction zone 120 may be substantially free of the different type of catalyst from the other reaction zone. For example, the isomerization reaction zone 110 may comprise less than 1 wt. % of the metathesis catalyst 122 from the metathesis reaction zone 120. Similarly, the metathesis reaction zone 120 may comprise less than 1 wt. % of the isomerization catalyst 112 from the isomerization reaction zone 110. Referring again to FIG. 1, in embodiments, the isomerization reaction zone 110 and the metathesis reaction zone 120 may be positioned directly against the other without an intervening separator.

Referring again to FIG. 1, various operating conditions are contemplated for contacting the feedstock 140 with the system 100. In embodiments, the feedstock 140 may contact the system 100 at a space hour velocity of from 10 per hour ($h^{-1}$) to 10,000 $h^{-1}$. For example, the feedstock 140 may contact the system 100 at a space hour velocity of from 10 $h^{-1}$ to 5000 $h^{-1}$, from 10 $h^{-1}$ to 2500 $h^{-1}$, from 10 $h^{-1}$ to 1200 $h^{-1}$, from 100 $h^{-1}$ to 10,000 $h^{-1}$, from 100 $h^{-1}$ to 5000 $h^{-1}$, from 100 $h^{-1}$ to 2500 $h^{-1}$, from 100 $h^{-1}$ to 1200 $h^{-1}$, from 300 $h^{-1}$ to 10,000 $h^{-1}$, from 300 $h^{-1}$ to 5000 $h^{-1}$, from 300 $h^{-1}$ to 2500 $h^{-1}$, from 300 $h^{-1}$ to 1200 $h^{-1}$, from 500 $h^{-1}$ to 10,000 $h^{-1}$, from 500 $h^{-1}$ to 5000 $h^{-1}$, from 500 $h^{-1}$ to 2500 $h^{-1}$, or from 500 $h^{-1}$ to 1200 $h^{-1}$. Furthermore, the feedstock 140 may contact the system 100 at a pressure of from 1 bar to 30 bars. For example, the feedstock 140 may contact the system 100 at a pressure of from 1 bar to 20 bars, from 1 bar to 10 bars, from 2 bars to 30 bars, from 2 bars to 20 bars, or from 2 bars to 10 bars. The feedstock 140 may also contact the system 100 at atmospheric pressure.

Optionally, prior to the introduction of the feedstock 140 to the system 100, the isomerization catalyst 112 and the metathesis catalyst 122 may be pretreated. For example, the catalysts in the system 100 may be pretreated by passing a heated gas stream through the system 100 for a pretreatment period. The gas stream may include one or more of an oxygen-containing gas, nitrogen gas ($N_2$), carbon monoxide (CO), hydrogen gas ($H_2$), a hydrocarbon gas, air, other inert gas, or combinations of these gases. The temperature of the heated gas stream may be from 250° C. to 700° C., from 250° C. to 650° C., from 250° C. to 600° C., from 250° C. to 500° C., from 300° C. to 700° C., from 300° C. to 650° C., from 300° C. to 600° C., from 300° C. to 500° C., from 400° C. to 700° C., from 400° C. to 650° C., from 400° C. to 600° C., or from 400° C. to 500° C. The pretreatment period may be from 1 minute to 30 hours, from 1 minute to 20 hours, from 1 minute to 10 hours, from 1 minute to 5 hours, from 0.5 hours to 30 hours, from 0.5 hours to 20 hours, from 0.5 hours to 10 hours, from 0.5 hours to 5 hours, from 1 hours to 30 hours, from 1 hour to 20 hours, from 1 hour to 10 hours, from 1 hour to 5 hours, from 5 hours to 30 hours, from 5 hours to 20 hours, or from 5 hours to 10 hours. For example, the system 100 may be pretreated with nitrogen gas at a temperature of 550° C. for a pretreatment period of from 1 hour to 5 hours before introducing the feedstock 140.

EXAMPLES

The various embodiments of isomerization catalysts, methods of making the isomerization catalysts, and methods of using the isomerization catalyst in the production of propene will be further clarified by the following examples. The examples are illustrative in nature, and should not be understood to limit the subject matter of the present disclosure.

Example 1—Hydrothermal Synthesis of Isomerization Catalyst

An isomerization catalyst was prepared using hydrothermal synthesis. In particular, 18.02 grams (g) of urea and 15.39 g of magnesium nitrate hexahydrate (Mg(NO$_3$)$_2$.6H$_2$O) were dissolved in 100 milliliters (mL) of deionized water (DI water) and stirred vigorously at room temperature for 1 hour to form a catalyst precursor solution. The catalyst precursor solution was then transferred to an autoclave and placed in an oven at 120° C. for 72 hours at a ramp rate of 1 degree Celsius per minute (° C./min). The resulting magnesium oxide precipitants were then filtered from the solution via vacuum filtration, dried overnight at room temperature, and them dried in a vacuum oven at 80° C. for 24 hours to form an isomerization catalyst. The isomerization catalyst was then calcined in a calcination oven under air at a ramping rate of 1° C./min until the isomerization catalyst attained a temperature of 550° C. The isomerization catalyst was then maintained in the calcination oven at a temperature of 550° C. for 5 hours. Following calcination, the isomerization catalyst was maintained in the calcination oven and allowed to slowly cool to room temperature. The isomerization catalyst prepared according to the above-described method is referred to subsequently as the catalyst of Example 1.

Example 2—Surfactant-Assisted Hydrothermal Synthesis of Isomerization Catalyst

An isomerization catalyst was prepared using surfactant-assisted hydrothermal synthesis. In particular, 18.02 g of urea and 15.39 g of magnesium nitrate hexahydrate were dissolved in 100 mL of deionized water and rapidly stirred at room temperature for 1 hour to form a first solution. Polyethylene glycol (PEG) was then added to the first solution such that the molar ratio of magnesium to polyethylene glycol was 1:0.03, and the first solution was stirred at room temperature for 2 hours to form a catalyst precursor solution. The catalyst precursor solution was then processed according to the same procedure previously described in Example 1 to form an isomerization catalyst. The isomerization catalyst prepared according to the above-described method is referred to subsequently as the catalyst of Example 2.

Example 3—Surfactant-Assisted Hydrothermal Fabrication of Isomerization Catalyst with pH Adjustment An isomerization catalyst was prepared using surfactant-assisted hydrothermal synthesis. In particular, 18.02 g of urea and 15.39 g of magnesium nitrate hexahydrate were dissolved in 100 mL of deionized water and rapidly stirred at room temperature for 1 hour to form a first solution. Polyethylene glycol was then added to the first solution such that the ratio of magnesium nitrate hexahydrate to polyethylene glycol was 1:0.03, and the first solution was stirred at room temperature for 2 hours to form a catalyst precursor solution. The pH of the catalyst precursor solution was then adjusted to a pH of 5 by the dropwise addition of acetic acid. The catalyst precursor solution was then processed according to the same procedure previously described in Example 1 to form an isomerization catalyst. The isomerization catalyst prepared according to the above-described method is referred to subsequently as the catalyst of Example 3.

Example 4—Surfactant-Assisted Hydrothermal Fabrication of Isomerization Catalyst with pH Adjustment An isomerization catalyst was prepared using surfactant-assisted hydrothermal synthesis. In particular, 18.02 g of urea and 15.39 g of magnesium nitrate hexahydrate were dissolved in 100 mL of deionized water and rapidly stirred at room temperature for 1 hour to form a first solution. Polyethylene glycol was then added to the first solution such that the ratio of magnesium nitrate hexahydrate to polyethylene glycol was 1:0.03, and the first solution was stirred at room temperature for 2 hours to form a catalyst precursor solution. The pH of the catalyst precursor solution was then adjusted to a pH of 9 by the dropwise addition of concentrated ammonium. The catalyst precursor solution was then processed according to the same procedure previously described in Example 1 to form an isomerization catalyst. The isomerization catalyst prepared according to the above-described method is referred to subsequently as the catalyst of Example 4.

Example 5—Surfactant-Assisted Hydrothermal Fabrication of Isomerization Catalyst with pH Adjustment An isomerization catalyst was prepared using surfactant-assisted hydrothermal synthesis. In particular, 18.02 g of urea and 15.39 g of magnesium nitrate hexahydrate were dissolved in 100 mL of deionized water and rapidly stirred at room temperature for 1 hour to form a first solution. Polyethylene glycol was then added to the first solution such that the ratio of magnesium nitrate hexahydrate to polyethylene glycol was 1:0.03, and the first solution was stirred at room temperature for 2 hours to form a catalyst precursor solution. The pH of the catalyst precursor solution was then adjusted to a pH of 11 by the dropwise addition of concentrated ammonium. The catalyst precursor solution was then then processed according to the same procedure previously described in Example 1 to form an isomerization catalyst. The isomerization catalyst prepared according to the above-described method is referred to subsequently as the catalyst of Example 5.

Comparative Example 6—Commercially-Available Magnesium Oxide Catalyst

An isomerization catalyst was prepared from a magnesium oxide base material, commercially available from Sigma Aldrich. The commercially-available magnesium oxide was dried overnight in a vacuum oven at 90° C. to form an isomerization catalyst. The isomerization catalyst was then calcined in a calcination oven under air at a ramping rate of 1° C./min until the isomerization catalyst attained a temperature of 550° C. The isomerization catalyst was then maintained in the calcination oven at a temperature of 550° C. for 5 hours. Following calcination, the isomerization catalyst was maintained in the calcination oven and allowed to slowly cool to room temperature. The isomerization catalyst prepared according to the above-described method is referred to subsequently as the catalyst of Comparative Example 6.

Example 7—Incipient Wetness Impregnation Synthesis of Metathesis Catalyst

A metathesis catalyst was prepared using incipient wetness impregnation synthesis. In particular, 0.157 g of ammonium metatungatate hydrate [(NH$_4$)$_6$H$_2$W$_{12}$O$_{40}$.xH$_2$O] was dissolved in 5 g of deionized water to form a first solution. It is noted that, in order to effectuate incipient wetness impregnation, the volume of the first solution corresponds to the total pore volume of the desired support material. The first solution was then added dropwise to 5 g of silica extrudates to form a metathesis catalyst. The metathesis catalyst was then dried overnight in a vacuum oven at 80° C. The metathesis catalyst was then calcined in a calcination oven under air at a ramping rate of 1° C./min until the magnesium oxide catalyst attained a temperature of 250° C. The metathesis catalyst was then maintained in the calcination oven at a temperature of 250° C. for 3 hours. The ramping rate of 1° C./min was then resumed until the metathesis catalyst attained a temperature of 550° C. The metathesis catalyst was then maintained in the calcination oven at a temperature of 550° C. for 8 hours. Following calcination, the metathesis catalyst was maintained in the calcination oven and allowed to slowly cool to room temperature. The resulting metathesis catalyst was determined to comprise 10 wt. % tungsten oxide and 90 wt. % silica by X-ray fluorescence (XRF) analysis. The metathesis catalyst prepared according to the above-described method is referred to subsequently as the catalyst of Example 7.

Example 8—Evaluation of Isomerization Catalyst Structures

Figure 3:
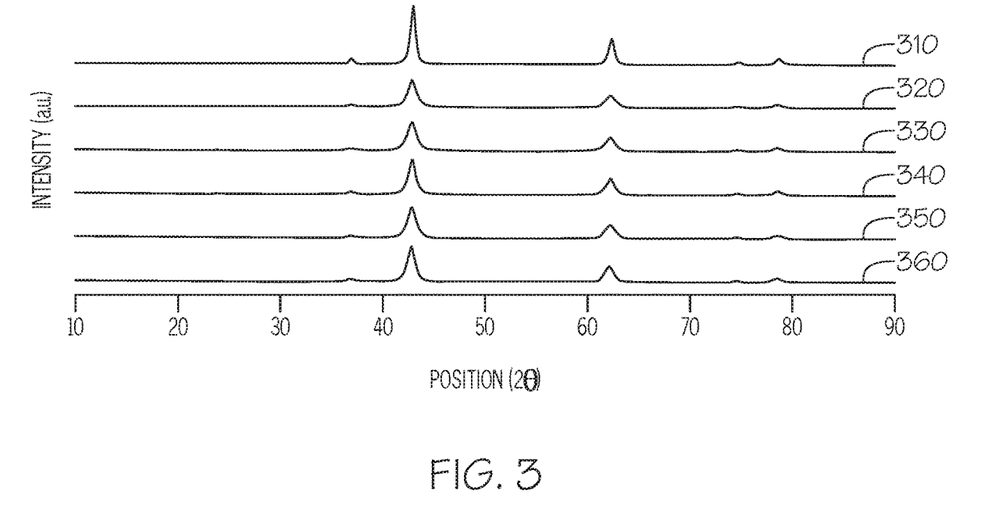
FIG. 3 graphically depicts the X-ray diffraction (XRD) profiles of isomerization catalysts, according to one or more embodiments of the present disclosure.

The crystallographic structures of the catalysts of Examples 1-5 were obtained from the measured XRD profiles of the catalysts. The XRD profiles of the catalyst of Example 1 (360), the catalyst of Example 2 (350), the catalyst of Example 3 (340), the catalyst of Example 4 (330), the catalyst of Example 5 (320), and the catalyst of Comparative Example 6 (310) are depicted in FIG. 3. The diffraction peaks corresponding to the cubic structure of magnesium oxide in a single phase may be observed in FIG. 3 at 2 Theta (2θ)=36 degrees)(°, 42°, 62°, 74°, and 78° for all examples. A comparison of the XRD profile of the commercially-available magnesium oxide catalyst with the XRD profiles of the catalysts of Examples 1-5 also indicates that the average particle size of the catalysts of Examples 1-5, as estimated by the Scherrer equation, are much smaller than the average particle size of the catalyst of Comparative Example 6. Additionally, a comparison of the XRD profiles of the catalysts of Examples 2-5 also indicates that the pH of the catalyst precursor solution has a negligible effect, if any, on the average particle size of the catalysts.

Example 9—Evaluation of Metathesis Catalyst Structure

Figure 4:
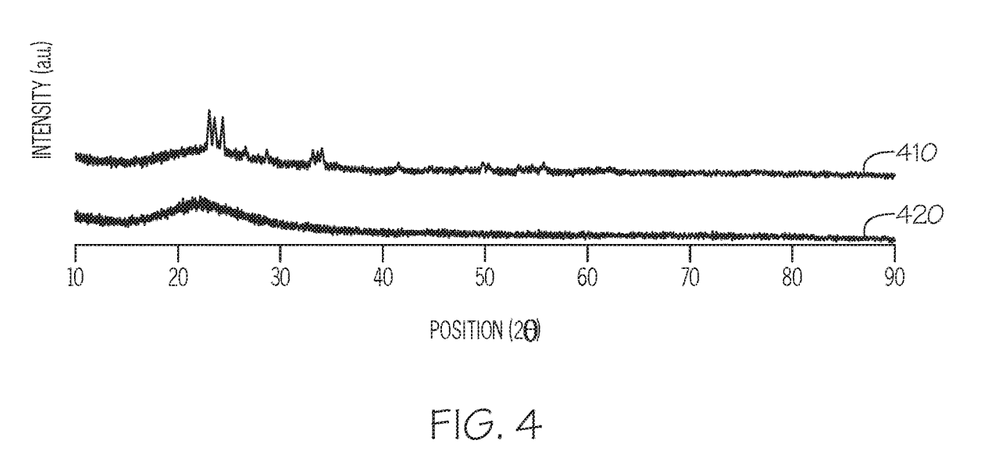
FIG. 4 graphically depicts the XRD profiles of a silica catalyst support before and after impregnation with tungsten oxide, according to one or more embodiments of the present disclosure.

The crystallographic structures of the catalyst of Example 6 were obtained from the measured XRD profiles of the catalyst before and after impregnation of the support material with tungsten oxide. The XRD profiles of the catalyst before impregnation (420) and after impregnation (410) are depicted in FIG. 4. The broad diffraction peaks corresponding to the silica support material may be observed in both XRD profiles. The diffraction peaks corresponding to the cubic structure of tungsten oxide may be observed in FIG. 4 at 2θ=23° and 33° only in the XRD profile of the catalyst after impregnation. This observation indicates the successful incorporation of tungsten oxide into the silica support material of the catalyst of Example 6.

Example 10—Evaluation of Catalyst Properties

The mechanical properties of the catalysts of Examples 1-5, and 7, as well as the catalyst of Comparative Example 6, were determined and provided in Table 1. In particular, the surface areas of the catalysts were determined by the Brunauer Emmett-Teller (BET) method, the cumulative volume of pores and the average pore width were determined by the Barrett, Joyner, and Halenda (BJH) method, and the average particle sizes were calculated by the Scherrer equation. The properties of the catalysts of Examples 1-5 and the catalyst of Comparative Example 6 are provided in Table 1.

TABLE 1

| | Catalyst Properties | | | |
|---|---|---|---|---|
| Catalyst | Surface Area ($m^2/g$) | Cumulative Volume of Pores ($cm^3/g$) | Average Pore Width (Å) | Average Particle Size (Å) |
| Comparative Example 6 | 60.49 | 0.30 | 184.41 | 991.91 |
| Example 1 | 124.47 | 0.22 | 70.35 | 482.06 |
| Example 2 | 144.64 | 0.23 | 61.14 | 414.81 |
| Example 3 | 132.00 | 0.25 | 75.22 | 454.51 |
| Example 4 | 219.81 | 0.31 | 56.13 | 272.97 |
| Example 5 | 159.16 | 0.23 | 57.06 | 376.99 |
| Example 7 (Before Impregnation) | 515.66 | 1.96 | 153.27 | 116.36 |
| Example 7 (After Impregnation) | 386.72 | 1.61 | 169.34 | 155.15 |

Example 11—Evaluation of Catalyst Performances

The catalysts of Examples 1-5, and 7, as well as the catalyst of Comparative Example 6, were tested for activity and selectivity for converting 1-butene to propene in a fixed-bed continuous flow reactor, such as the reactor depicted in FIG. 2, at atmospheric pressure. The activity and selectivity of each catalyst were tested in a dual catalyst system that included the catalyst of Example 6. A fixed amount of 0.1 g of each catalyst was pressed and sieved to a desired particle size in the range of 250-300 microns (μm), and was packed into a reactor tube directly above 0.1 g of the catalyst of Example 6. Layers of silicon carbide were positioned both upstream and downstream of the catalysts in order to ensure that the catalysts remained within the desired isothermal range.

Each reactor was first heated to 160° C. under nitrogen at a flow rate of 120 milliliters per minute (mL/min) and argon at a flow rate of 6 mL/min for 24 hours in order to ensure slow moisture desorption from the catalysts and identify any potential gas leaks from the reactors. The catalysts were then activated under nitrogen at 550° C. and a flow rate of 120 mL/min for 24 hours. The catalysts were then cooled to 300° C. under nitrogen before a feedstock of 1-butene was passed through the reactors at a flow rate of 0.0079 grams per minute (g/min) and a weight hourly space velocity (WHSV) of 4.725 per hour ($h^{-1}$) for 18 hours. Quantitative analysis of the products for each reactor was performed using a gas chromatograph (commercially available as Agilent GC-7890B) with a thermal conductivity detector (TCD) and two flame ionization detectors (FID).

Figure 5:
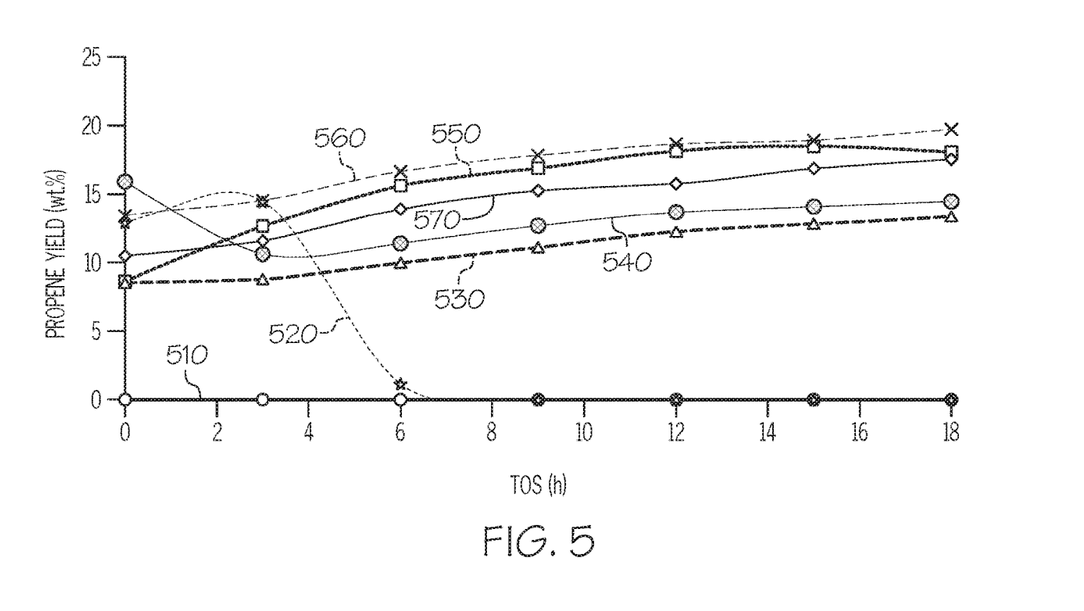
FIG. 5 graphically depicts the propene yield (y-axis) as a function of time-on-stream (TOS) (y-axis) obtained from a reactor for converting a butene-containing feedstock to propene, according to one or more embodiments of the present disclosure.

The propene yield as a function of time on stream (TOS) for reactors comprising the catalyst of Example 1 (530), the catalyst of Example 2 (540), the catalyst of Example 3 (550), the catalyst of Example 4 (560), the catalyst of Example 5 (570), the catalyst of Comparative Example 6 (520), and the catalyst of Example 7 alone (510) are depicted in FIG. 5. As shown by FIG. 5, the reactor comprising only the catalyst of Example 7 did not produce propene. This indicates insufficient isomerization activity at a temperature of 300° C. and, as a result, the formation of insufficient amounts of 2-butene from the feedstock of 1-butene necessary for metathesis. Additionally, as shown by FIG. 5, the production of propene rapidly decreased in the reactor comprising the commercially-available magnesium oxide catalyst. This indicates that the catalyst of Comparative Example 6 is not stable at temperatures of 300° C. and quickly deactivates. The total conversions and yields obtained by each reactor is summarized in Table 2.

TABLE 2

Catalyst Performances at 300° C.

| Catalyst | 1-Butene Conversion % | Propene Selectivity | Yield (wt. %) | | | | | | | |
|---|---|---|---|---|---|---|---|---|---|---|
| | | | Ethylene | Propene | 1-Butene | 2-Butene (Trans) | 2-Butene (Cis) | $C_5$ | $C_6$ | $C_7$ |
| Example 1 + Example 7 | 87 | 15.5 | 0.3 | 13.4 | 13.5 | 32.1 | 21.0 | 17.4 | 2.1 | 0.1 |
| Example 2 + Example 7 | 90 | 16.6 | 0.4 | 15.0 | 10.0 | 31.7 | 21.3 | 18.6 | 2.7 | 0.3 |
| Example 3 + Example 7 | 89 | 20.3 | 0.7 | 18.1 | 10.9 | 27.0 | 17.7 | 20.0 | 4.6 | 0.9 |
| Example 4 + Example 7 | 89 | 22.1 | 0.9 | 19.8 | 10.8 | 24.8 | 16.4 | 20.1 | 5.7 | 1.3 |
| Example 5 + Example 7 | 88 | 19.9 | 0.6 | 17.6 | 11.9 | 27.3 | 17.8 | 19.6 | 4.2 | 0.7 |
| Comparative Example 6 + Example 7 | 63 | 0.2 | 0.0 | 0.1 | 37.0 | 31.7 | 30.9 | 0.2 | 0.0 | 0.0 |
| Example 7 | 56 | 0.1 | 0.0 | 0.0 | 43.8 | 26.5 | 29.5 | 0.1 | 0.1 | 0.0 |

Example 12—Evaluation of Catalyst Thermal Stability

The catalysts of Examples 1-5, as well as the catalyst of Comparative Example 6, were tested for activity and selectivity for converting 1-butene to propene in a fixed-bed continuous flow reactor, such as the reactor depicted in FIG. 2, at atmospheric pressure. The activity and selectivity of each catalyst were tested according to the same procedure previously described in Example 11, however the catalysts were only cooled to an operational temperature of 400° C. and a feedstock of 1-butene was passed through the reactors for 45 hours.

Figure 6:
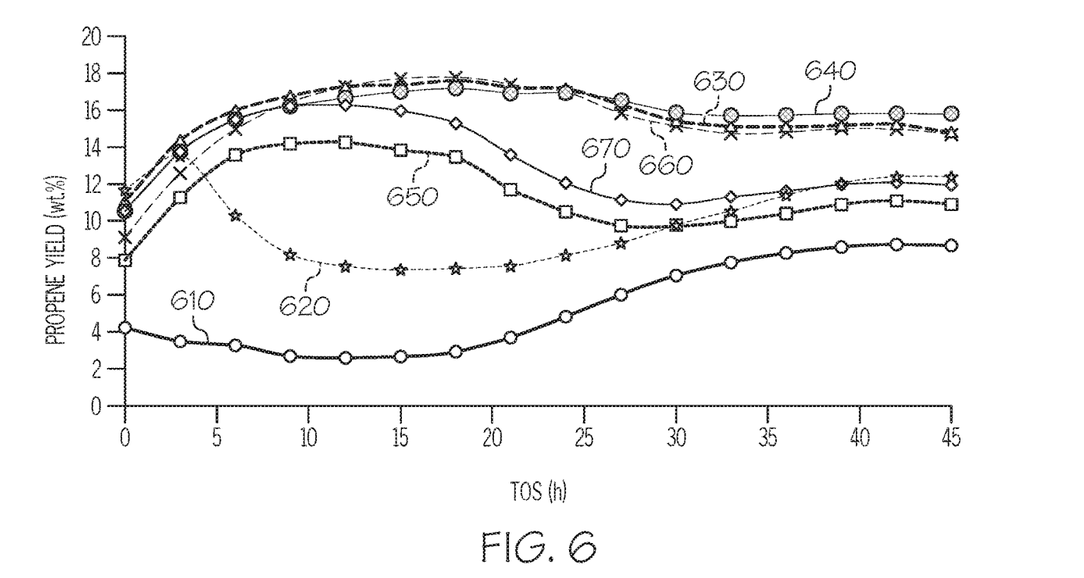
FIG. 6 graphically depicts the propene yield (y-axis) as a function of time-on-stream (TOS) (y-axis) obtained from a reactor for converting a butene-containing feedstock to propene, according to one or more embodiments of the present disclosure.

The propene yield as a function of time on stream (TOS) for reactors comprising the catalyst of Example 1 (630), the catalyst of Example 2 (640), the catalyst of Example 3 (650), the catalyst of Example 4 (660), the catalyst of Example 5 (670), the catalyst of Comparative Example 7 (620), and the catalyst of Example 7 alone (610) are depicted in FIG. 6. As depicted by FIG. 6, the reactor comprising only the catalyst of Example 6 was capable of producing propene. This indicates that the isomerization activity of the catalyst of Example 6 is sufficient to produce the 2-butene necessary for metathesis from a feedstock of 1-butene at a temperature of 400° C. The total conversions and yields obtained by each reactor is summarized in Table 3.

TABLE 3

Catalysts Performances at 400° C.

| Catalyst | 1-Butene Conversion % | Propene Selectivity | Yield (wt. %) | | | | | | | |
|---|---|---|---|---|---|---|---|---|---|---|
| | | | Ethylene | Propene | 1-Butene | 2-Butene (Trans) | 2-Butene (Cis) | $C_5$ | $C_6$ | $C_7$ |
| Example 1 + Example 7 | 84 | 17.0 | 0.6 | 14.3 | 15.8 | 28.1 | 20.2 | 17.1 | 3.1 | 0.5 |
| Example 2 + Example 7 | 88 | 17.9 | 0.6 | 15.7 | 12.1 | 28.0 | 20.6 | 18.6 | 3.5 | 0.6 |
| Example 3 + Example 7 | 82 | 13.7 | 0.5 | 11.2 | 18.2 | 30.5 | 22.5 | 14.1 | 2.5 | 0.3 |
| Example 4 + Example 7 | 84 | 17.0 | 0.6 | 14.2 | 16.2 | 28.0 | 20.1 | 17.0 | 3.2 | 0.5 |
| Example 5 + Example 7 | 82 | 14.6 | 0.5 | 12.0 | 17.7 | 30.0 | 21.7 | 15.0 | 2.6 | 0.3 |
| Comparative Example 6 + Example 7 | 78 | 17.0 | 1.4 | 13.3 | 21.6 | 23.8 | 18.0 | 16.1 | 5.1 | 0.6 |
| Example 7 | 76 | 11.6 | 1.6 | 8.8 | 23.8 | 27.9 | 21.4 | 10.8 | 5.0 | 0.5 |

Example 13—Evaluation of Amount of Catalyst

Figure 7:
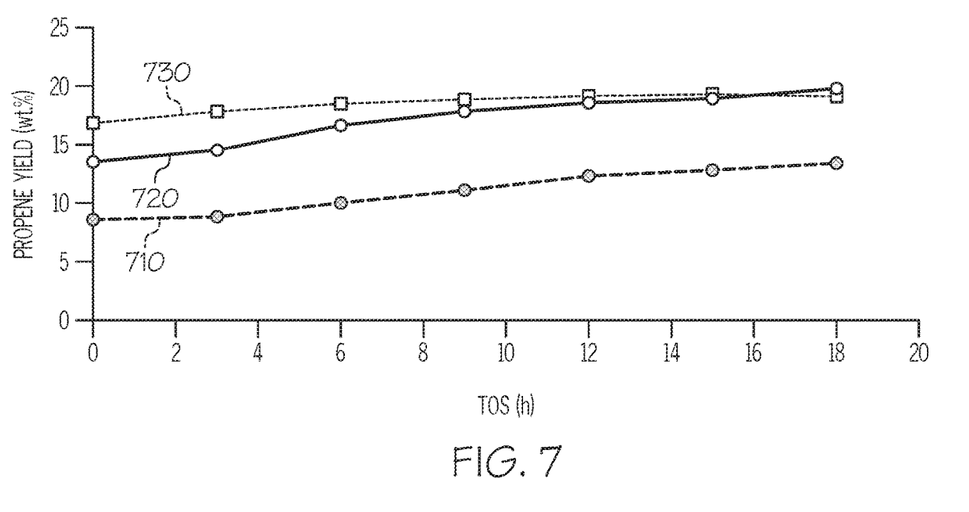
FIG. 7 graphically depicts the propene yield (y-axis) as a function of time-on-stream (TOS) (y-axis) obtained from a reactor for converting a butene-containing feedstock to propene, according to one or more embodiments of the present disclosure.

The catalysts of Example 1 and Example 4 were tested for activity and selectivity for converting 1-butene to propene in a fixed-bed continuous flow reactor, such as the reactor depicted in FIG. 2, at atmospheric pressure. The activity and selectivity of each catalyst were tested according to the same procedure previously described in Example 10; however, an additional reactor containing double (i.e., 0.2 g) of the catalyst of Example 1 was also tested. The propene yield as a function of time on stream (TOS) for reactors comprising the catalyst of Example 1 (710), the catalyst of Example 4 (720), and double the amount of the catalyst of Example 1 (730) are depicted in FIG. 7. As depicted by FIG. 7, isomerization catalysts prepared by surfactant-assisted hydrothermal synthesis and, in particular, surfactant-assisted hydrothermal synthesis with an adjusted pH yield similar or superior amounts of propene as unmodified isomerization catalysts while requiring only half the amount.

It will be apparent to those skilled in the art that various modifications and variations can be made without departing from the spirit or scope of the disclosure. Since modifications, combinations, sub-combinations and variations of the disclosed embodiments incorporating the spirit and substance of the disclosure may occur to persons skilled in the art, the scope of the disclosure should be construed to include everything within the scope of the appended claims or their equivalents.

In a first aspect of the present disclosure, a method of producing an isomerization catalyst may comprise preparing a catalyst precursor solution comprising at least a magnesium precursor, a hydrolyzing agent, and polyethylene glycol; hydrothermally treating the catalyst precursor solution to produce a magnesium oxide precipitant; and calcining the magnesium oxide precipitant to produce the isomerization catalyst.

A second aspect of the present disclosure may comprise the first aspect where the molar ratio of the magnesium precursor to the hydrolyzing agent in the catalyst precursor solution is from 1:10 to 1:1.

A third aspect of the present disclosure may comprise either of the first or second aspects where the molar ratio of the magnesium precursor to polyethylene glycol in the catalyst precursor solution is from 1:0.01 to 1:0.1.

A fourth aspect of the present disclosure may comprise any of the first through third aspects further comprising adjusting the pH of the catalyst precursor solution.

A fifth aspect of the present disclosure may comprise the fourth aspect where the pH of the catalyst precursor solution is adjusted to a pH of from 3 to 7.

A sixth aspect of the present disclosure may comprise the fourth aspect where the pH of the catalyst precursor solution is adjusted to a pH of from 8 to 12.

A seventh aspect of the present disclosure may comprise any of the first through sixth aspects where hydrothermally treating the catalyst precursor solution comprises heating the catalyst precursor solution to a temperature of from 100° C. to 140° C. for a duration of from 48 hours to 96 hours.

An eighth aspect of the present disclosure may comprise any of the first through seventh aspects where calcining the catalyst precipitant comprises heating the catalyst precipitant to a temperature of from 450° C. to 650° C. for a duration of from 1 hour to 10 hours.

A ninth aspect of the present disclosure may comprise as isomerization catalyst made by the method of any of the first through eighth aspects.

A tenth aspect of the present disclosure may comprise the ninth aspect where the surface area of the isomerization catalyst is from 125 $m^2/g$ to 225 $m^2/g$.

An eleventh aspect of the present disclosure may comprise either of the ninth or tenth aspects where the average particle size of the isomerization catalyst is from 20 nm to 50 nm.

In a twelfth aspect of the present disclosure, a method of producing propene from a butene-containing feedstock may comprise contacting the butene-containing feedstock with an isomerization catalyst to produce an isomerization reaction effluent, the isomerization catalyst prepared by a method comprising: preparing a catalyst precursor solution comprising at least a magnesium precursor, a hydrolyzing agent, and polyethylene glycol; hydrothermally treating the catalyst precursor solution to produce a magnesium oxide precipitant; and calcining the magnesium oxide precipitant to produce the isomerization catalyst; and contacting the isomerization reaction effluent with a metathesis catalyst to produce propene, where the metathesis catalyst is disposed in a metathesis reaction zone downstream of the isomerization catalyst.

A thirteenth aspect of the present disclosure may comprise the twelfth aspect where the isomerization catalyst is disposed in an isomerization reaction zone.

A fourteenth aspect of the present disclosure may comprise either of the twelfth or thirteenth aspects where contacting the butene-containing feedstock with the isomerization catalyst causes the isomerization of at least a portion of the butene-containing feedstock.

A fifteenth aspect of the present disclosure may comprise any of the twelfth through fourteenth aspects where the molar ratio of the magnesium precursor to the hydrolyzing agent in the catalyst precursor solution is from 1:10 to 1:1.

A sixteenth aspect of the present disclosure may comprise any of the twelfth through fifteenth aspects where the molar ratio of the magnesium precursor to polyethylene glycol in the catalyst precursor solution is from 1:0.01 to 1:0.1.

A seventeenth aspect of the present disclosure may comprise any of the twelfth through sixteenth aspects further comprising adjusting the pH of the catalyst precursor solution.

An eighteenth aspect of the present disclosure may comprise the seventeenth aspect where the pH of the catalyst precursor solution is adjusted to a pH of from 3 to 7.

A nineteenth aspect of the present disclosure may comprise the seventeenth aspect where the pH of the catalyst precursor solution is adjusted to a pH of from 8 to 12.

A twentieth aspect of the present disclosure may comprise any of the twelfth through nineteenth aspects where hydrothermally treating the catalyst precursor solution comprises heating the catalyst precursor solution to a temperature of from 100° C. to 140° C. for a duration of from 48 hours to 96 hours.

A twenty-first aspect of the present disclosure may comprise any of the twelfth through twentieth aspects where calcining the catalyst precipitant comprises heating the catalyst precipitant to a temperature of from 450° C. to 650° C. for a duration of from 1 hour to 10 hours.

A twenty-second aspect of the present disclosure may comprise any of the twelfth through twenty-first aspects where the surface area of the isomerization catalyst is from 125 $m^2/g$ to 225 $m^2/g$.

A twenty-third aspect of the present disclosure may comprise any of the twelfth through twenty-second aspects where the average particle size of the isomerization catalyst is from 20 nm to 50 nm.

It should now be understood that various aspects of the present disclosure are described and such aspects may be utilized in conjunction with various other aspects.

It is noted that one or more of the following claims utilize the term "where" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A method of producing an isomerization catalyst, the method comprising:
   preparing a catalyst precursor solution comprising at least a magnesium precursor, a hydrolyzing agent, and polyethylene glycol, where the molar ratio of the magnesium precursor to polyethylene glycol in the catalyst precursor solution is from 1:0.01 to 1:0.1;
   hydrothermally treating the catalyst precursor solution to produce a magnesium oxide precipitant; and
   calcining the magnesium oxide precipitant to produce the isomerization catalyst.

2. The method of claim 1, where the molar ratio of the magnesium precursor to the hydrolyzing agent in the catalyst precursor solution is from 1:10 to 1:1.

3. The method of claim 1, further comprising adjusting the pH of the catalyst precursor solution.

4. The method of claim 3, where the pH of the catalyst precursor solution is adjusted to a pH of from 3 to 7.

5. The method of claim 3, where the pH of the catalyst precursor solution is adjusted to a pH of from 8 to 12.

6. The method of claim 1, where hydrothermally treating the catalyst precursor solution comprises heating the catalyst precursor solution to a temperature of from 100° C. to 140° C. for a duration of from 48 hours to 96 hours.

7. The method of claim 1, where the surface area of the isomerization catalyst is from 125 $m^2/g$ to 225 $m^2/g$.

* * * * *